(12) United States Patent
Trayhan, Jr. et al.

(10) Patent No.: US 10,024,823 B2
(45) Date of Patent: Jul. 17, 2018

(54) EVALUATING CONDITION OF COMPONENTS USING ACOUSTIC SENSOR IN LIGHTING DEVICE

(71) Applicant: General Electric Company, Schenectady, NY (US)

(72) Inventors: David Terry Trayhan, Jr., Greenville, SC (US); Hua Zhang, Greer, SC (US)

(73) Assignee: General Electric Company, Schenectady, NY (US)

(*) Notice: Subject to any disclaimer, the term of this patent is extended or adjusted under 35 U.S.C. 154(b) by 140 days.

(21) Appl. No.: 15/206,382

(22) Filed: Jul. 11, 2016

(65) Prior Publication Data

US 2018/0011059 A1    Jan. 11, 2018

(51) Int. Cl.

| | |
|---|---|
| *G01N 29/22* | (2006.01) |
| *G01H 1/00* | (2006.01) |
| *G01M 13/02* | (2006.01) |
| *G01N 29/11* | (2006.01) |
| *G01N 29/12* | (2006.01) |
| *G01N 29/14* | (2006.01) |
| *G01N 29/24* | (2006.01) |
| *G01N 29/44* | (2006.01) |
| *G01N 29/46* | (2006.01) |
| *G01N 29/48* | (2006.01) |

(Continued)

(52) U.S. Cl.
CPC ............ *G01N 29/22* (2013.01); *G01H 1/006* (2013.01); *G01M 13/028* (2013.01); *G01N 29/11* (2013.01); *G01N 29/12* (2013.01); *G01N 29/14* (2013.01); *G01N 29/223* (2013.01); *G01N 29/2475* (2013.01); *G01N 29/4454* (2013.01); *G01N 29/46* (2013.01); *G01N 29/48* (2013.01); *H04R 1/028* (2013.01); *H05B 33/0803* (2013.01); *H05B 37/0227* (2013.01); *G01N 2291/2693* (2013.01)

(58) Field of Classification Search
CPC ........ G01N 29/22; G01N 29/07; G01N 29/11; G01N 29/12; G01N 29/14; G01N 29/24; G01N 29/44; G01N 29/46; G01N 29/48; G01N 29/223; G01N 29/2475; G01N 29/4454

See application file for complete search history.

(56) References Cited

U.S. PATENT DOCUMENTS

| | | | | |
|---|---|---|---|---|
| 4,955,005 A | * | 9/1990 | Loeffelman | A01K 79/00 116/22 A |
| 5,282,178 A | * | 1/1994 | Hill | A01K 79/02 367/141 |

(Continued)

*Primary Examiner* — Helen Kwok
(74) *Attorney, Agent, or Firm* — Ernest G. Cusick; Hoffman Warnick LLC (57) ABSTRACT

Aspects of the disclosure include systems, methods, and program products for evaluating the condition of a component using an acoustic sensor embedded within a lighting device. A system according to the present disclosure can include a first lighting device configured to illuminate an area of an industrial plant; a first acoustic sensor embedded within the first lighting device and configured to detect an acoustic signature of a component in the industrial plant; a computing device communicatively connected to the first acoustic sensor and configured to evaluate a condition of the component in the industrial plant based on the acoustic signature.

20 Claims, 5 Drawing Sheets

(51) Int. Cl.
*H04R 1/02* (2006.01)
*H05B 33/08* (2006.01)
*H05B 37/02* (2006.01)

(56) References Cited

U.S. PATENT DOCUMENTS

| | | | | |
|---|---|---|---|---|
| 5,291,858 A * | 3/1994 | Patrick | ............... | A01K 79/02 |
| | | | | 119/230 |
| 6,388,949 B1 * | 5/2002 | Lenhardt | ............... | A01K 79/02 |
| | | | | 116/22 A |
| 9,010,356 B2 | 4/2015 | Adler et al. | | |
| 2004/0122602 A1 * | 6/2004 | Nagase | ............... | G01M 1/225 |
| | | | | 702/51 |
| 2007/0160373 A1 * | 7/2007 | Biegelsen | ......... | H05B 37/0245 |
| | | | | 398/118 |
| 2009/0196016 A1 * | 8/2009 | Massara | ............ | F21V 23/0471 |
| | | | | 362/86 |
| 2010/0295473 A1 * | 11/2010 | Chemel | ............... | H05B 37/029 |
| | | | | 315/294 |
| 2013/0238256 A1 | 9/2013 | Anup et al. | | |
| 2013/0321245 A1 | 12/2013 | Harper | | |
| 2015/0039250 A1 * | 2/2015 | Rank | .............. | H04R 29/00 |
| | | | | 702/56 |
| 2015/0222495 A1 * | 8/2015 | Mehta | ................ | G06F 3/0484 |
| | | | | 715/736 |
| 2015/0241871 A1 | 8/2015 | Yoshino et al. | | |
| 2015/0260557 A1 | 9/2015 | DeSilva et al. | | |
| 2015/0260611 A1 | 9/2015 | DeSilva et al. | | |
| 2017/0006201 A1 * | 1/2017 | Segura | ................ | G01N 29/14 |
| 2017/0027045 A1 * | 1/2017 | Chemel | ................ | G05B 15/02 |

* cited by examiner

EVALUATING CONDITION OF COMPONENTS USING ACOUSTIC SENSOR IN LIGHTING DEVICE

BACKGROUND

The disclosure relates generally to evaluating the condition of one or more components in an industrial plant using an acoustic sensor embedded in a lighting device.

An industrial plant may include one or more machines including several interconnected components, and various properties of the industrial plant can be derived from conditions of these individual components. Examples of industrial plants can include power plants (e.g., combustion-based power plants including a fleet of gas turbines and/or other machines therein), manufacturing facilities, chemical processing and/or treatment facilities (e.g., refineries), recycling plants, smelting facilities, mills, etc. In the example of a combustion-based power plant, gas turbine assemblies therein can generate mechanical energy by combusting a source of fuel intermixed with compressed air. These combustion reactions create mechanical power for driving a load component attached to the combustion-based power source (e.g., by a rotatable shaft).

The effectiveness of combustion-based power plants and/or other types of machines in an industrial plant can depend on their implementation, environment, and/or other factors such as manufacturing quality and state of operation (e.g., transient state or steady state). In addition, several user-driven and environmental factors can affect the performance of components in an industrial plant, including the magnitude of intended energy output, efficiency or condition of individual components, and estimates of part and/or system lifespan. Some systems may apply various forms of computing technology to evaluate the status and operation performance of distinct systems or components in an industrial plant.

SUMMARY

A first aspect of the disclosure provides a system including: a first lighting device configured to illuminate an area of an industrial plant; a first acoustic sensor embedded within the first lighting device and configured to detect an acoustic signature of a component in the industrial plant; a computing device communicatively connected to the first acoustic sensor and configured to evaluate a condition of the component in the industrial plant based on the acoustic signature.

A second aspect of the disclosure provides a method for evaluating components in an industrial plant, the method including: detecting an acoustic signature of a component in the industrial plant with a first acoustic sensor included within a first lighting device of industrial plant; determining a difference between a baseline acoustic signature and an acoustic signature of a component in the industrial plant; identifying the component from a plurality of components based on at least the acoustic signature and a position of the first lighting device; and evaluating a condition of the component based on the position of the component and the difference between the acoustic signature the baseline acoustic signature.

A third aspect of the invention provides a program product stored on a computer readable storage medium for evaluating components in an industrial plant, the computer readable storage medium comprising program code for causing a computer system to: determine a difference between a baseline acoustic signature and an acoustic signature of a component in the industrial plant, the acoustic signature of the component being detected by a first acoustic sensor included within a first lighting device of the industrial plant; identify the component from a plurality of components based on at least the acoustic signature and a position of the first lighting device; and evaluate a condition of the component based on the position of the component and the difference between the acoustic signature the baseline acoustic signature.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be used and that changes may be made without departing from the scope of the present teachings. The following description is, therefore, merely exemplary.

Where an element or layer is referred to as being "on," "engaged to," "disengaged from," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Embodiments of the present disclosure provide systems, program products, and methods for evaluating components in an industrial plant. In an example embodiment, a system according to the present disclosure can include at least one lighting device configured to illuminate a particular area of an industrial plant. The lighting device can include, e.g., a conventional electrical-mechanical connection configured for attachment to a conventional lightbulb fixture, such as a threaded lightbulb socket. In other embodiments, the lighting device can include an industrial lamp of any desired size configured to be connected to an electrical ballast. In still other embodiments, the lighting device can include any currently known or later developed illumination mechanism such as an incandescent lightbulb, a light emitting diode (LED), a gas discharge lamp, etc. Such lighting devices may be manufactured to include other elements of the present disclosure within a single housing of the lighting device.

In embodiments of the present disclosure, each lighting device in an industrial plant can include an acoustic sensor embedded therein. During operation, the acoustic sensor in the lighting device can detect an acoustic signature produced by one or more components in a particular area of the industrial plant. A computing device, communicatively connected to the acoustic sensor of the lighting device, can evaluate a condition of the component of the industrial plant based on one or more properties of the detected acoustic signatures. In alternative embodiments, the computing device of the system can be wholly or partially embedded within at least one of the lighting devices. Embedding acoustic sensors and/or computing devices within lighting devices can provide greater accessibility and functionality to managers of an industrial plant, e.g., by permitting a user to access an application, web-portal, etc., immediately after such lighting devices are installed to analyze or view acoustic signatures detected by each acoustic sensor.

Figure 1:
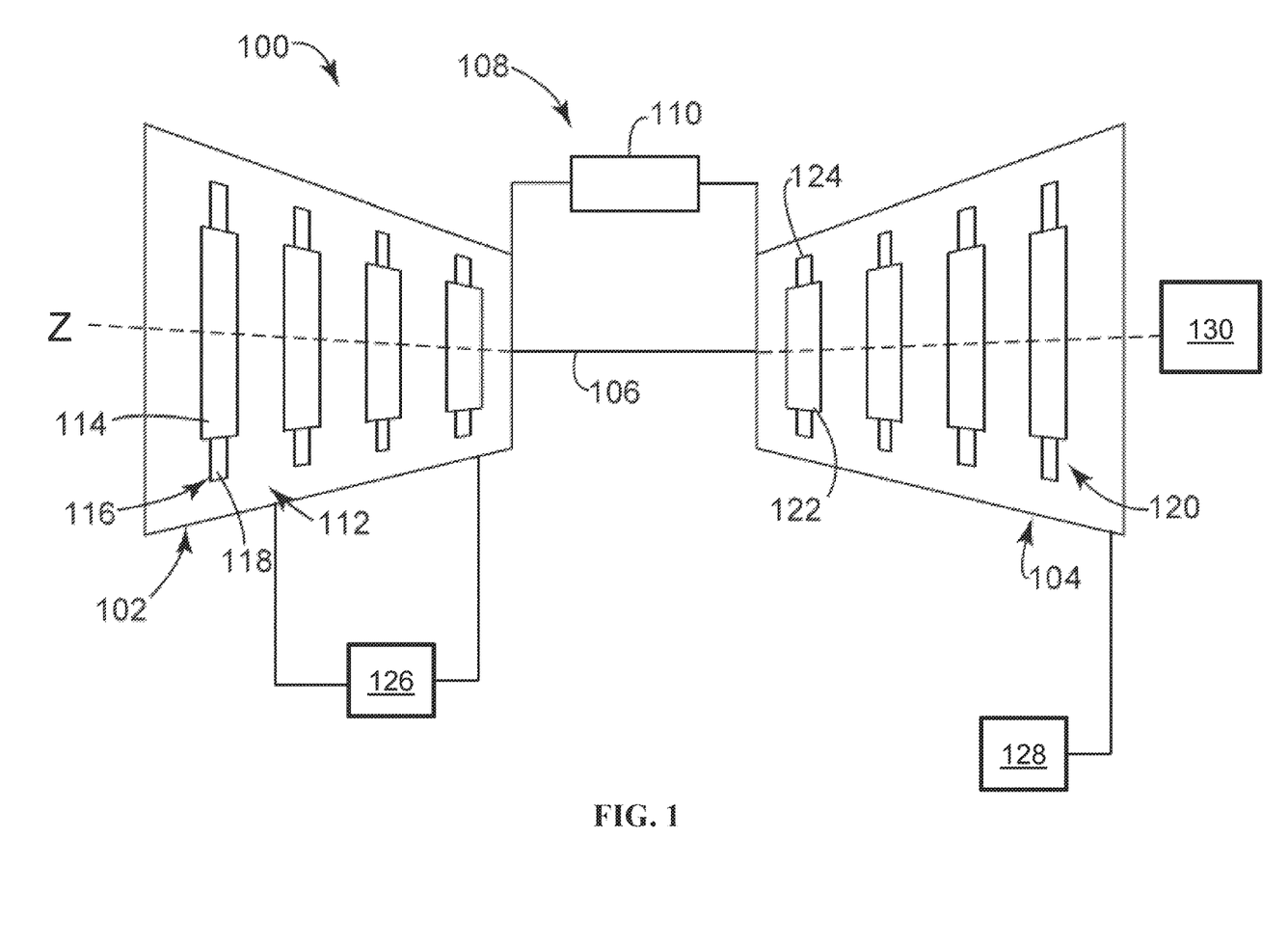
FIG. 1 provides a schematic view of an industrial plant in the form of a gas turbine, FIG. 2 provides a schematic view of a system according to embodiments of the present disclosure.

FIG. 1 shows a turbomachine 100, which may be included within an industrial plant as discussed elsewhere herein. Turbomachine 100 can include, e.g., a compressor 102 operatively coupled to a turbine 104 through a shared compressor/turbine shaft 106. Turbomachine 100 is depicted as being in the form of a gas turbine in FIG. 1, but it is understood that other types of machines (e.g., steam turbines, water turbines, etc.) can be substituted for, or used with, gas turbines and/or deployed in the same industrial plant in embodiments of the present disclosure. More generally, any machine which includes an embodiment of turbine 104 can be used, modified, and/or controlled to yield embodiments of the present disclosure as discussed herein. Compressor 102 can be fluidically connected to turbine 104, e.g., through a combustor assembly 108. Each combustor assembly 108 can include one or more combustors 110. Combustors 110 may be mounted to turbomachine 100 in a wide range of configurations including, but not limited to, being arranged in a can-annular array. Compressor 102 includes a plurality of compressor rotor wheels 112. Compressor rotor wheels 112 include a first stage compressor rotor wheel 114 having a plurality of first stage compressor rotor blades 116 each having an associated airfoil portion 118. Similarly, turbine component 104 includes a plurality of turbine wheel components 120 including one or more rotor wheels 122 having a set of corresponding turbine rotor blades 124.

During operation, an operative fluid such as a cot busted hot gas can flow from combustor(s) 110 into turbine 104. The operative fluid in turbine 104 can pass over multiple rotor blades 124 mounted on turbine wheel 122 and arranged in a group of successive stages. The first set of turbine blades 124 coupled to wheel 122 and shaft 106 can be identified as a "first stage" of turbomachine 100, with the next set of turbine blades 124 being identified as a "second stage" of turbomachine 100, etc., up to the last set of turbine blades 124 in a final stage of turbomachine 100. The final stage of turbomachine 100 can include the largest size and/or highest radius turbine blades 124 in turbomachine 100. A plurality of respective nozzles (not shown) can be positioned between each stage of turbomachine 100 to further define a flow path through turbomachine 100. The operative fluid flowing over each turbine blade 124 can rotate blades 124 by imparting thermal and mechanical energy thereto, thereby rotating shaft 106 of turbomachine 100. Turbomachine 100 may also include one or more auxiliary components such as valves 126, e.g., to modulate the operative fluid flow out of and into the direct flow path for various purposes, e.g., to be used in one or more pump/motor sets 128 also included within turbomachine 100. Rotating shaft 106 can generate power by being mechanically coupled to a generator component 130 which converts mechanical energy of shaft 106 into electrical energy for powering devices connected to generator 130. The amount of electrical energy produced by generator 130 can be measured, e.g., in Joules (J) and/or Watts (W) as an amount of work and/or power produced by turbomachine 100.

Figure 2:
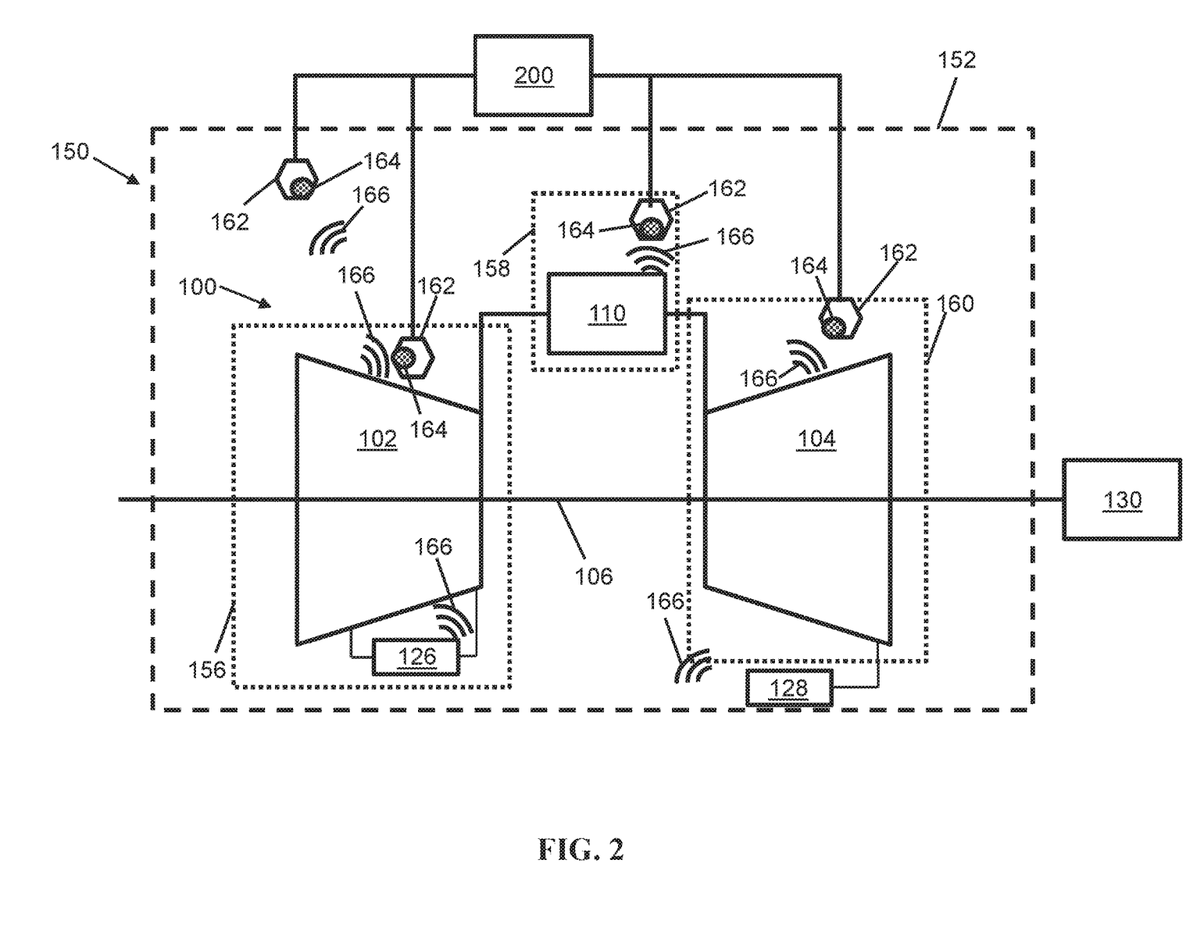

Turning to FIG. 2, a system 150 for evaluating the condition of machines in an industrial plant according to embodiments of the present disclosure is shown. System 150 can include an industrial plant 152, which as noted elsewhere herein can include, e.g., power plants (e.g., combustion-based power plants including a fleet of gas turbines and/or other machines therein), manufacturing facilities, chemical processing and/or treatment facilities (e.g., refineries), recycling plants, smelting facilities, mills, etc. System 150 and industrial plant 152 are described herein with industrial plant 152 being in the form of a power plant including one or more assemblies therein, such as turbomachine(s) 100 and components thereof (e.g., compressor 102, turbine 104, combustor 110, valves 126, pump/motor sets 128, etc., hereinafter "component(s) 102, 104, 110, 126, 128"). Although component(s) 102, 104, 110, 126, 128 are discussed throughout the present disclosure as an example, it is understood that system 150 can be configured to evaluate the condition of any number of predetermined components within turbomachine 100 and/or other machines within industrial plant 152. Each component 102, 104, 110, 126, 128 of turbomachine 100 within industrial plant 152 can be housed in a respective area 156, 158, 160 and/or other areas or sub-areas of industrial plant 152 not explicitly identified or described. Turbomachine 100 is shown by example to include compressor component 102 and valve 126 in first area 156, combustor 110 in second area 158, turbine component 104 in third area 160 and pump/motor set 128 in a fourth unenclosed or unidentified area. Each area 156, 158, 160 can be separated by architectural features such as partitions, floors, signage, etc., and/or can refer to areas within a shared room, space, building, etc. In some cases, component(s) 102, 104, 110, 126, 128 of one turbomachine 100 may be in close proximity with each other, but may be separated from similar component(s) 102, 104, 110, 126, 128 in other turbomachines. Thus, component(s) 102, 104, 110, 126, 128 shown in FIG. 2 may be part of a single turbomachine 100 or alternatively may each be portions of respective separate turbomachines 100. It is also understood that areas 156, 158, 160 can be defined solely by whether they are illuminated with one or more corresponding lighting devices 162, e.g., where all components 102, 104, 110, 126, 128 of industrial plant 152 are housed in a single room. Areas 156, 158, 160 can include multiple components 102, 104, 110, 126, 128 therein in alternative embodiments.

A group of lighting devices 162, depicted with a hexagonal outline, can be installed in industrial plant 152 to provide illumination. Each lighting devices 162 can illuminate one or more respective areas 156, 158, 160 of industrial plant 152. As discussed elsewhere herein, each lighting device 162 can be provided in the form of any currently-known or later-developed electrically powered lighting instrument and as examples can include incandescent lamps, gas-discharge lamps, and/or LED lamps powered by an electric current. More particularly, each lighting device 162 can be configured to interface with one or more conventional electric light sockets for transmitting electric current to lighting device(s) 162 through a corresponding electrical and/or mechanical coupling.

The electric current for powering lighting devices 162 (which can be generated with generator 130 and/or other devices for generating electricity and electrically coupled to industrial plant 152) can simultaneously power an acoustic sensor 164 embedded within lighting device(s) 162. Acoustic sensor 164 can be included as part of, e.g., an integrated circuit (IC) device which includes electrical connections for powering lighting device 162 and/or acoustic sensor 164 based on internal signal processing logic. The integrated circuit (IC) would also include a communications mechanism, for example ethernet over power, WIFI or cellular, to transmit measured data outside of the device. One embodiment of system 150 according to the present disclosure can include lighting devices 162 in the form of LED lamps each including one or more acoustic sensors 164 embedded therein. Acoustic sensor(s) 164 can be provided in the form of, e.g., a microphone, a surface acoustic wave sensor, a seismometer, and/or other types of sensors considered to be acoustic, vibrational, and/or sound sensors. In addition, acoustical sensors 164 may incorporate varying types of base technologies, e.g., capacitive, fiber-optic, piezoelectric, electret, acoustical wave, and/or other systems for measuring and/or detecting acoustic inputs.

Acoustic sensor(s) 164 can be embedded within lighting device(s) 162 by being of smaller size than lighting device(s) 162, and being embedded therein during manufacture. Embedding acoustic sensor(s) 164 within one or more lighting devices 162 can allow acoustic sensor(s) 164 to be powered by the same electric current delivered to lighting device(s) 162. Each lighting device 162 is depicted in FIG. 2 as having only one acoustic sensor 164, but other embodiments of the present disclosure can include lighting devices 162 which include multiple acoustic sensors 164. Acoustic sensor(s) 164 can be configured to detect acoustic signatures 166. As described herein, an "acoustic signature" refers to a one or more sound waves detected with acoustic sensor(s) 164 generated by one or more respective components 102, 104, 110, 126, 128. Acoustic signature 166 can be represented analytically as a singular or composite sound wave having varied frequencies, amplitudes, and/or other properties based on the underlying source(s) of acoustic signature 166. Each acoustic signature 166 can originate from one or more sources in industrial plant 152 during operation, such that several acoustic signatures 166 detected within industrial plant 152 each have a set of frequencies, wavelengths, amplitudes, phases, etc., when plotted as a sound wave.

System 100 can include a computing device 200 communicatively coupled to one or more lighting devices 162 and acoustic sensors 164 to perform various functions, including the evaluation of components 102, 104, 110, 126, 128 of industrial plant 152 as described herein. Computing device 200 can generally include any type of computing device capable of performing operations by way of a processing component (e.g., a microprocessor) and as examples can include a computer, computer processor, electric and/or digital circuit, and/or a similar component used for computing and processing electrical inputs. Example components and operative functions of controller 160 are discussed in detail elsewhere herein. One or more acoustic sensors 164 may also include an integrated circuit to communicate with and/or wirelessly transmit signals to computing device 200. Each acoustic sensor 164 may also include a receiver (not shown) of microwave energy for power sensor circuits therein. Acoustic sensor(s) 164, as integrated into the lighting device 162, may include an integrated circuit unit for the modulation of received acoustic signatures 166 into particular frequency signals so they can be transmitted through the same electrical/mechanical connection socket for the lighting device 162, as discussed elsewhere herein.

Computing device 200 can evaluate the condition of components 102, 104, 110, 126, 128 of industrial plant 152 by analyzing acoustic signatures 166 detected with acoustic sensor(s) 164. For example, acoustic sensor(s) 164 may detect acoustic signatures 166 generated by each component 102, 104, 110, 126, 128 in a given area 156, 158, 160 of industrial plant 152. Computing device 200 may include software thereon for processing acoustic signatures 166 representative of predetermined components 102, 104, 110, 126, 128 to be evaluated during operation. For example, computing device 200 may include software for extracting individual soundwaves from acoustic signature 166 by application of one or more currently known or later developed acoustical analysis techniques, e.g., Fourier Transform application, Fast Fourier Transform (FFT) application, linear prediction, wave filtration (e.g., high pass filtration, low pass filtration, and/or bandpass filtration), analysis of spectrograms (i.e., plots of frequency and intensity over time), etc. Such analyses may be performed by computing device 200 automatically and/or with the aid of user inputs. It is also understood that in some cases, computing device 200 can evaluate the condition of components 102, 104, 110, 126, 128 of industrial plant 152 using acoustic signatures 166 directly and/or in combination with processes described herein for analyzing extracted and/or modified acoustic signatures 166.

In an embodiment, computing device 200 can compare acoustic signatures 166 detected with acoustic sensor(s) 164 with one or more baseline acoustic signatures (stored, e.g., as data within computing device 200) to evaluate the condition of component(s) 102, 104, 110, 126, 128. As used herein a "baseline acoustic signature" generally refers to a predetermined representation of one or more sounds having respective amplitudes, frequencies, wavelengths, phases, etc. Baseline acoustic signatures used in the comparison can be based on the operation of a different industrial plant 152, or can be derived from past operation of industrial plant 152 and/or previously detected acoustic signatures 166. Computing device 200 can compare acoustic signatures 166 to baseline acoustic signatures by determining whether an amplitude, frequency, and/or other property of detected acoustic signatures 166 exceeds a tolerance window of the baseline acoustic signature. For example, a volume of acoustic signatures 166 produced by combustor 110 of turbomachine 100 may have a predicted acoustic volume within industrial plant 152 of approximately twenty decibels (dB) during steady state operation. A corresponding tolerance window for the volume of combustor 110 can be, e.g., twenty-five dB to reflect variances during operation caused by routine fluctuations. In the event that combustor 110 produces acoustic signatures 166 much higher volume, e.g., thirty decibels (dB), acoustic signature 166 will include a volume which exceeds one tolerance window of turbomachine 100. In addition, computing device 200 can be configured to apply multiple tolerance windows for a given acoustic signature 166 to evaluate the condition of component(s) 102, 104, 110, 126, 128. Such evaluations can vary based on, e.g., the baseline acoustic signature used, and/or decisions initiated by a user of computing device 200. In one example, computing device 200 can determine whether component(s) 102, 104, 110, 126, 128 require servicing, replacement, etc., based on whether an amplitude of acoustic signature(s) 166 exceed a baseline acoustic signature for component(s) 102, 104, 110, 126, 128 by a predetermined number of dB. In another embodiment, computing device 200 can determine whether component(s) 102, 104, 110, 126, 128, are possibly defective or at risk of failure, e.g., based on whether acoustic signatures 166 include wavelengths which exceed the tolerance window of one or more wavelengths in a baseline acoustic signature, thereby indicating that unusual sounds have been produced regardless of their volume. It is also understood that computing device 200 can implement other acoustical analyses separately or in combination to perform several evaluations of component(s) 102, 104, 110, 126, 128 sequentially or simultaneously. For example, computing device 200 may implement an acoustical pattern analysis of the industrial plant 152 due to reverberation in an enclosed space. As used herein, the term "defective" refers to any unit which fails to conform with at least one predetermined operating requirement, e.g., efficiency, acoustic volume during operation, maximum internal pressure, maximum material stress or strain, minimum or maximum start-up and/or shutdown time, etc.

In some cases, computing device 200 can combine its analysis of acoustic signature(s) 166 with a positional analysis of other data to identify unknown component(s) 102, 104, 110, 126, 128, within industrial plant 152 which produce anomalous sounds within acoustic signature(s) 166. For example, where detected acoustic signature(s) 166 include anomalous soundwaves produced by an unknown component 102, 104, 110, 126, 128, computing device 200 can identify one or more specific acoustic sensors 164 and/or areas 156, 158, 160 where such sounds were detected. Computing device 200 can cross-reference these determinations with positional data of industrial plant 152 to identify one or more components 102, 104, 110, 126, 128 within industrial plant 152 which may have produced the anomalous sounds in acoustic signature 166. For example, computing device 200 can determine that two acoustic signatures 166 detected by two acoustic sensors 164 detected soundwaves with an amplitude exceeding a baseline amplitude for a particular operation. Computing device 200 can then determine that the two acoustic sensors 164 are proximal to, e.g., area 156 but acoustically isolated from areas 158, 160 of industrial plant 152. Computing device 200 can then derive a source of the anomalous sound by triangulating the position two or more acoustic sensors 164 with component 102 and/or a subcomponent thereof within area 156 of industrial plant 152. In some cases, possible sources of the anomalous sound(s) in acoustic signature(s) 166 can be ruled out by comparing characteristic properties of the anomalous sound(s) with example frequencies, amplitudes, etc., of baseline acoustic signatures. Where one or more acoustic sensors 164 are direction-sensitive (e.g., by including one or more directional microphones therein), computing device 200 can further locate and/or identify components 102, 104, 110 126, 128 which correspond to acoustic signature(s) 166 based on the directional orientation and/or sensitivity of each acoustic sensor 164.

System 150 can combine the acoustic analyses described herein with other currently-known or later-developed systems which evaluate components 102, 104, 110, 126, 128 of industrial plant 152 based on the operating attributes of an assembly within industrial plant 152. As used herein, an "assembly" can include any machine or portion thereof which includes two or more components 102, 104, 110, 126, 128 and in an example embodiment can include the entirety of turbomachine 100 and/or a portion thereof. Operating attributes of an assembly can include, e.g., the amount of power generated during operation, the stress and/or wear experienced by the assembly and its components over time, an emissions output, temperature and/or flow rate, etc. System 150 can interface with other systems, e.g., by including other analysis systems within computing device 200 and/or permitting computing device(s) 200 to exchange data with other systems for evaluating component(s) 102, 104, 110, 126, 128 based on operating attributes of an assembly. For example, acoustic sensors) 164 may detect acoustic signature 166 with a frequency which exceeds the tolerance window of a baseline acoustic signature. As a result, computing device 200 of system 150 may determine that one or more components 102, 104, 110, 126, 128 within industrial plant 152 could be defective, as defined elsewhere herein. Computing device 200 can then further analyze other operating attributes of component(s) 102, 104, 110, 126, 128 which produced the anomalous sound to determine whether one or more component(s) 102, 104, 110, 126, 128 within industrial plant 152 are unsafe, performing below user-specified expectations or requirements, in need of servicing, etc. It is also understood that computing device 200 can analyze one or more operating attributes of component(s) 102, 104, 110, 126, 128 before applying an acoustic analysis, or that both analyses may be carried out in parallel and/or substantially simultaneously.

Figure 3:
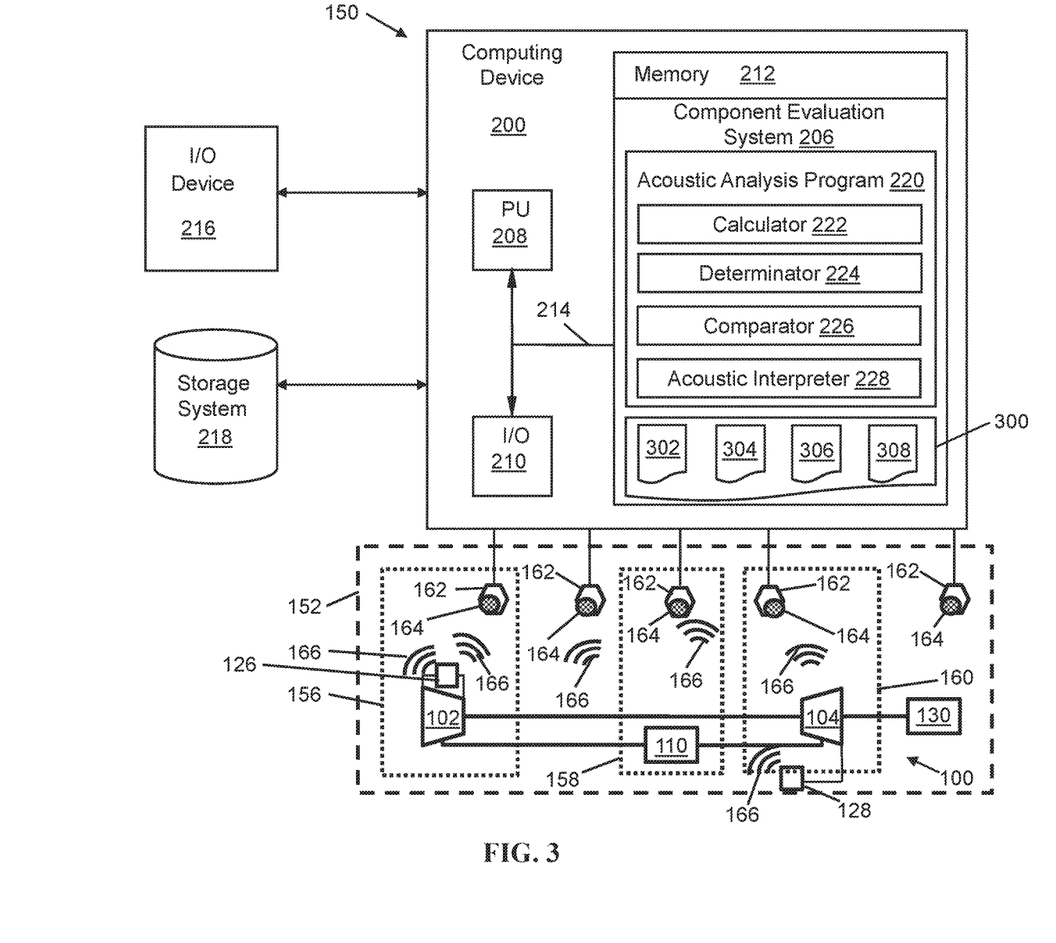
FIG. 3 provides a schematic view of an illustrative environment including a computing device for implementing a system according to embodiments of the present disclosure.

To further illustrate the operational features and details of system 150, an illustrative embodiment of computing device 200 is discussed herein. Referring to FIGS. 2 and 3 together, an example embodiment of system 150 and computing device 200 and sub-components thereof is illustrated with a simplified depiction of industrial plant 152. In particular, system 150 can include computing device 200, which in turn can include a component evaluation system 206. The configuration shown in FIG. 3 is one embodiment of a system for evaluating a component 102, 104, 110, 126, 128 of a machine within industrial plant 152. As discussed herein, computing device 200 can analyze the various acoustic signatures 166 detected with acoustic sensors 164 to evaluate the condition of components 102, 104, 110, 126, 128 within industrial plant 152. Furthermore, embodiments of the present disclosure can perform these functions automatically and/or responsive to user input by way of an application accessible to a user or other computing device. Such an application may, e.g., exclusively provide the functionality discussed herein and/or can combine embodiments of the present disclosure with a system, application, etc., for remotely controlling lighting device(s) 162. Embodiments of the present disclosure may be configured or operated in part by a technician, computing device 200, and/or a combination of a technician and computing device 200. It is understood that some of the various components shown in FIG. 3 can be implemented independently, combined, and/or stored in memory for one or more separate computing devices that are included in computing device 200. Further, it is understood that some of the components and/or functionality may not be implemented, or additional schemas and/or functionality may be included as part of component evaluation system 206.

Computing device 200 can include a processor unit (PU) 208, an input/output (I/O) interface 210, a memory 212, and a bus 214. Further, computing device 200 is shown in communication with an external I/O device 216 and a storage system 218. Component evaluation system 206 can execute an acoustic analysis program 220, which in turn can include various software components configured to perform different actions, including a calculator 222, a determinator 224, a comparator 226, and an acoustic interpreter 228. Acoustic interpreter 228 can implement any currently known or later developed acoustic analysis technique (including those specifically referenced herein). For example, acoustic interpreter 228 can convert acoustic signatures) 166 detected with acoustic sensor 164 into a waveform representation, and then extract and/or divide the waveform one or more individual sound waves pertaining to particular components 102, 104, 110, 126, 128 etc., areas 156, 158, 160, etc. Acoustic interpreter 228 can thereby implement one or more acoustic conversion and/or analysis techniques to implement one or more of the process steps described herein.

The various modules of component evaluation system 206 can use algorithm-based calculations, look up tables, and similar tools stored in memory 212 for processing, analyzing, and operating on data to perform their respective functions. In general, PU 208 can execute computer program code to run software, such as control system 206, which can be stored in memory 212 and/or storage system 214. While executing computer program code, PU 208 can read and/or write data to or from memory 212, storage system 218, and/or I/O interface 210. Bus 214 can provide a communications link between each of the components in computing device 200. I/O device 216 can comprise any device that enables a user to interact with computing device 200 or any device that enables computing device 200 to communicate with the equipment described herein and/or other computing devices. I/O device 216 (including but not limited to keyboards, displays, pointing devices, etc.) can be coupled to controller 160 either directly or through intervening I/O controllers (not shown).

Memory 212 can also include various forms of data 300 pertaining to one or more acoustic signatures 166 and/or components 102, 104, 110, 126, 128 of industrial plant 152, such as those included within turbomachine 100. As discussed elsewhere herein, computing device 200 can evaluate the condition of component(s) 102, 104, 110, 126, 128 based on acoustic signatures 166 through operating steps which in turn can rely upon various forms of data 300. To exchange data between computer system 200 and acoustic sensors 164, computer system 200 can be in communication with acoustic sensor(s) 164 through any currently known or later developed type of communications network. For example, computer system 200 can be embedded at least partially within lighting device 162 as a component thereof, or can be embodied as a remotely located device such as a tablet, PC, smartphone, etc., in communication with acoustic sensor(s) 164 through any combination of wireless and/or wired communication protocols. To evaluate the condition of component(s) 102, 104, 110, 126, 128 of industrial plant 152, acoustic analysis program 220 of component evaluation system 206 can store and interact with data 300 according to processes of the present disclosure.

Data 300 can be organized into a group of fields. For example, data 300 can also include a positional data field 302 which includes one or more sets of data pertaining to the relative position of each component 102, 104, 110, 126, 128 within industrial plant 152. Positional data field 302 can include relative and/or absolute coordinates for each component, directional orientation data for each acoustic sensor 164, positional data for each lighting device 162, geometry data of plant 152, and/or other types of data relevant to locating one or more components 102, 104, 110, 126, 128 of industrial plant 152 relative to others. Other forms of data 300 can be provided in an operating attribute field 304 which includes one or more operating attributes pertaining to industrial plant 152 and/or assemblies which include components 102, 104, 110, 126, 128. Baseline acoustic signatures used in comparing steps to evaluate the condition of components 102, 104, 110, 126, 128 can be recorded in a baseline signature field 306. A tolerance window field 308 can include one or more tolerance windows from respective baseline acoustic signatures (stored, e.g., in baseline signature field 306) to which acoustic signatures 166 are compared to evaluate the condition of component(s) 102, 104, 106, 126, 128. More specifically, each entry of tolerance window field 308 can include a respective set of boundary values for frequency, wavelength, magnitude, etc., for baseline acoustic signatures compared with acoustic signature(s) 166 detected with acoustic sensor(s) 164. Each entry of fields 302, 304, 306, 308 can he indexed relative to time such that a user can cross-reference information of each field 302, 304, 306, 308 in data 300. It is also understood that data 300 can include other data fields and/or other types of data therein for evaluating the condition of components 102, 104, 110, 126, 128 of industrial plant 152.

Data 300 can also be subject to preliminary processing by modules of acoustic analysis program 220 before being recorded in one or more of fields 302, 304, 306, 308. For example, acoustic interpreter 228 can apply a set of rules to interpret the anomalous sounds of acoustic signatures) 166 from components 102, 104, 110, 126, 128. Such rules and/or other criteria may be generated from the manufacturer's design analysis of these components. For example, compressor 102 may generate acoustical energy particularly related to the number of rotating blades of various stages. In the case of combustor 110, the possible resonant frequencies, as related to the type and geometry of combustor 110, operating conditions, type of fuels combusted, etc., may be analyzed in design stage. Such analyses can determine criteria such as the amplitude limits associated with each frequency for acoustic signatures 166 to be stored in data 300.

Computing device 200 can comprise any general purpose computing article of manufacture for executing computer program code installed by a user (e.g., a personal computer, server, handheld device, etc.). However, it is understood that computing device 200 is only representative of various possible equivalent computing devices that may perform the various process steps of the disclosure. In addition, computing device 200 can be part of a larger system architecture operable to evaluate components 102, 104, 110, 126, 128.

To this extent, in other embodiments, computing device 200 can comprise any specific purpose computing article of manufacture comprising hardware and/or computer program code for performing specific functions, any computing article of manufacture that comprises a combination of specific purpose and general purpose hardware/software, or the like. In each case, the program code and hardware can be created using standard programming and engineering techniques, respectively. In one embodiment, computing device 200 may include a program product stored on a computer readable storage device, which can be operative to automatically evaluate components 102, 104, 110, 126, 128 of industrial plant 152 when executed.

Figure 4:
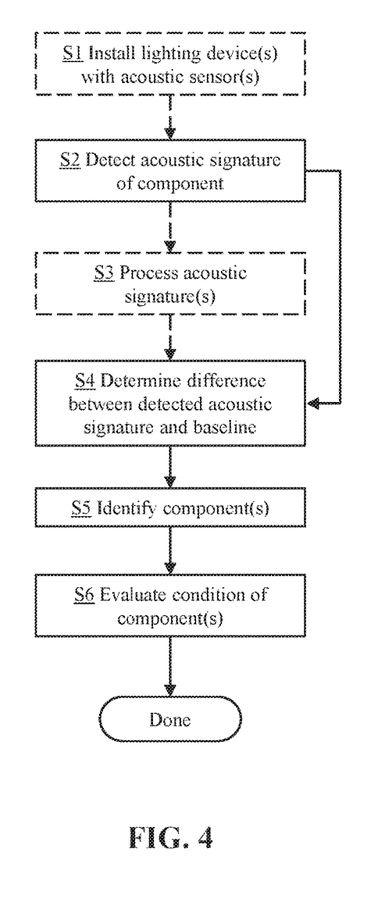
FIG. 4 provides an illustrative flow diagram of a method according to embodiments of the present disclosure.

Referring to FIGS. 2-4 together, steps for evaluating the condition of components within industrial plant 152 according to embodiments of the present disclosure are shown. The steps shown in FIG. 4 and described herein provide a general process overview for implementing embodiments of the present disclosure, and are discussed by reference to a group of illustrative examples. In addition, the process flow illustrated in FIG. 4 can be implemented, e.g., by way of system(s) 150 including computing device(s) 200 communicatively connected to lighting devices 162 each acoustic sensor(s) 164 embedded therein. It is understood that the various processes described herein can be implemented in real time during operation of turbomachine 100 and/or can be implemented as part of a historical analysis of turbomachine 100 (e.g., a post-failure or post-servicing analysis). One or more lighting devices 162 which include embedded acoustic sensors 164 can be installed within industrial plant 152 at step S1, e.g., by electrically and mechanically coupling each lighting device 162 to a conventional electrical socket provided within industrial plant 152. As described elsewhere herein, each electrical socket can include, e.g., an electrically conductive socket configured to mechanically engage and transmit electrical current to lighting device(s) 162 and the embedded acoustic sensor(s) 164. Lighting device(s) 162 can be installed by a party implementing the various process steps described herein and/or another party before processes of the present disclosure are implemented. As such, step S1 is shown in phantom to indicate that step S1 may be a preliminary step which occurs before other processes according to the present disclosure.

At step S2, each acoustic sensor 164 can detect corresponding acoustic signatures 166 originating from component(s) 102, 104, 110 of industrial plant 152. Each detected acoustic signature 166 can include a plurality of individual sounds generated by a plurality of a plurality of individual sources. Acoustic signatures 166 detected in step S2 can also be isolated sound waves generated by a single component or portion thereof, e.g., where acoustic sensor(s) 164 are positioned in an area 156, 158, 160 of industrial plant 152 where only one component 102, 104, 110, 126, 128 or portion thereof is located. Where acoustic sensor(s) 164 of lighting device(s) 162 detect acoustic signatures 166 originating from multiple sources and/or where noise (i.e., external acoustic signatures generated by sources other than component(s) 102, 104, 110, 126, 128 of industrial plant 152) contaminates acoustic signature(s) 166, the flow can optionally proceed to step S3 (shown in phantom) of processing acoustic signature(s) 166 detected in step S2 with computing device 200. The processing of acoustic signatures 166 can include using acoustic interpreter 228 of acoustic analysis program 220 to perform actions including, e.g., splitting each acoustic signature 166 into multiple acoustic signatures 166 to be stored in memory 212 (e.g., as data 300), filtering acoustic waves with particular frequencies, amplitudes, etc., for removal, converting or simplifying acoustic signature(s) 166 into various waveform representations, etc.

Processes for evaluating components 102, 104, 110, 126, 128 of industrial plant can include determining differences between each detected acoustic signature 166 and one or more baseline acoustic signatures in step S4. The determining in step S4 can be implemented by applying calculator 222 to each acoustic signature to calculate differences in one or more representative variables, in addition to applying calculator 222 to determining an amount by which one or more properties of acoustic signature(s) 166 differ from baseline acoustic signatures stored in baseline signature field 306. Each baseline acoustic signature used as a basis for comparison in step S4 can be included in memory 212 of computing device 200, and more specifically may be stored in data 300 as part of baseline signature field 302. Baseline acoustic signatures stored in baseline signature field 302 can be represented by the user of any currently known or later-developed mechanism for quantifying and/or representing one or more acoustic signatures, e.g., a could representation with a predetermined number of dimensions (e.g., a three-dimensional or four-dimensional point cloud for managing and visualizing large sets of data). Where one or more baseline acoustic signatures represent a non-defective performance of component(s) 102, 104, 110, 126, 128, a significant difference between acoustic signature(s) 166 and a baseline acoustic signature at step S4 can indicate, e.g., that one or more component(s) 102, 104, 110, 126, 128 may be defective. In other situations, a significant difference between acoustic signature(s) 166 and baseline acoustic signatures in step S4 can indicate other properties of component(s) 102, 104, 110, 126, 128 e.g., being degraded, damaged by unforeseen events, previously repaired or replaced, etc.

Methods according to the present disclosure can include identifying one or more components 102, 104, 110, 126, 128 represented in acoustic signature(s) 166 at step S5. The identifying in step S5 can be based on, e.g., the results of other process steps and/or other attributes, including attributes stored within memory 212 of computing device 200. As discussed elsewhere herein, acoustic interpreter 228 can process acoustic signature(s) 166 by identifying, extracting, simplifying, and/or otherwise transforming acoustic signatures 166 detected with acoustic sensors 164. Acoustic interpreter 228 at step S5 can cross reference one or more acoustic signature(s) 166 with information provided in positional data field 304, to locate a source of acoustic signature(s) 166 such as one or more component(s) 102, 104, 110, 126, 128. For example, acoustic interpreter 228 of acoustic analysis program 220 can isolate one or more sound waves in acoustic signature(s) 166 by unknown component(s) 102, 104, 110, 126, 128. Comparator 226 can compare the isolated sound waves to a baseline sample of sounds produced by compressor 102 (stored, e.g., in baseline signature field 306), and determinator 224 can determine whether the isolated sound is likely generated by a specific component in the group, e.g., compressor 102, turbine 104, combustor 110, valve 126, pump/motor set 128, etc. Calculator 222 and/or acoustic interpreter 228 can also identify the source of acoustic signatures) 166 by performing a positional analysis on acoustic signature(s) 166 and data 300, which in some cases may include triangulating a position and/or orientation of each lighting device 162 and acoustic sensor 164 in industrial plant 152 with a calculated, projected or estimated source of acoustic signature 166. The identified component(s) yielded from step S5 can be stored within memory 212 of computing device 200, e.g., as a form of data 300 optionally within positional data field 304.

At step S6, one or more elements of component evaluation system 206 can evaluate the condition of component(s) 102, 104, 110, 126, 128 which produced acoustic signal(s) 166. Component evaluation system 206 can evaluate the condition of component(s) 102, 104, 110, 126, 128 within industrial plant 152 based on the difference(s) determined in step S4 and/or other properties of industrial plant 152. For example, component evaluation system 206 may determine at step S4 that one or more acoustic signatures 166 differ significantly from baseline acoustic signatures produced by a non-defective component. Where component evaluation system 206 also identifies the component as being, e.g., compressor 102, determinator 224 can determine whether the difference between acoustic signature 166 and its respective baseline acoustic signature indicates a possible defect in compressor 102. The evaluated condition of compressor 102 can then be stored, e.g., within memory 212 of computing device 200. The flow can then conclude ("Done"), and the various process steps discussed herein can be repeated, modified, continued in parallel, etc., in response to user instructions or automatic settings of component evaluation system 206.

Figure 5:
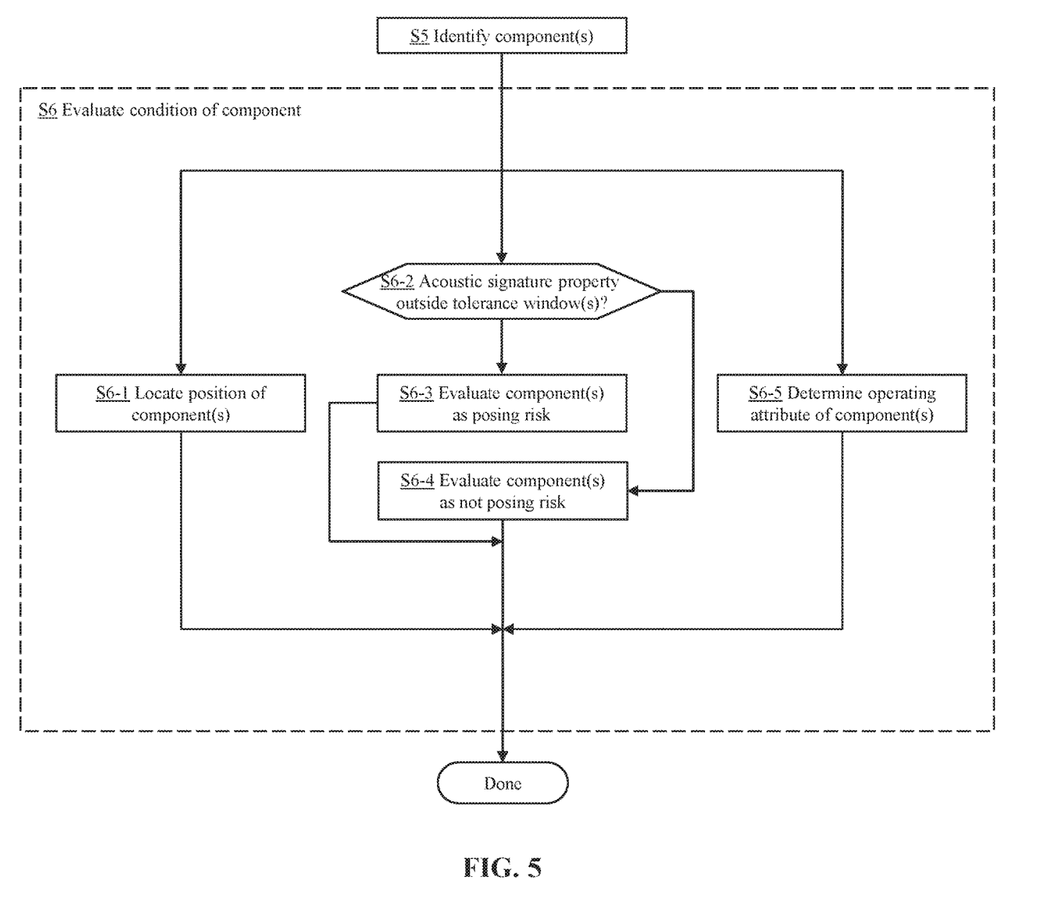
FIG. 5 provides an illustrative flow diagram with processes for evaluating the condition of a component according to embodiments of the present disclosure.

Referring to FIGS. 2-3 and 5, embodiments of the present disclosure can include an alternative and/or expanded group of process steps for implementing step 56, discussed elsewhere herein. At step S6-1, component evaluation system 206 can locate the position of one or more component(s) 102, 104, 106, 126, 128 within industrial plant 152 after identifying component(s) 102, 104, 110, 126, 128 for analysis in step S5. The located positions in step S6-1 can be expressed relative to other components within industrial plant 152, other fixtures and/or items of interest within industrial plant 152, and/or a set of predetermined coordinates. The locating of components 102, 104, 110, 126, 128 in step S6-1 can optionally be performed concurrently with and/or as part of step S5, discussed elsewhere herein. As also discussed elsewhere herein, locating the position of component(s) 102, 104, 110, 126, 128 in step S6-1 can include triangulating two or more lighting device 162 and/or acoustic sensors 164 with one or more component(s) 102, 104, 110, 126, 128 by application of data 300 stored in positional data field 304.

Embodiments of the present disclosure can include comparing at least one property of detected acoustic signature(s) 166 with one or more tolerance windows of a baseline acoustic signature in step S6-2. Comparator 226 of acoustic analysis program 220 can implement the comparing discussed herein, and the baseline acoustic signatures used in the comparison can be the same or different baseline acoustic signatures applied in step S4 (FIG. 4). The properties used in the comparison can include, e.g., the difference determined in step S2 (FIG. 4), an amplitude and/or frequency of acoustic signature 166, and/or other properties. The comparing in step S6-2 can include executing multiple comparisons between acoustic signature(s) 166 and respective tolerance windows, and evaluating component(s) 102, 104, 110, 126, 128 based on the tolerance windows being used in a particular comparison. Where the compared properties are outside the tolerance window(s) (i.e., "yes" at step S6-2), the flow can proceed to step S6-3 where component evaluation system 220 evaluates component(s) 102, 104, 110, 126, 128 as posing a risk (e.g., including a possible defect, being in need of service or replacement, etc.) Where the compared properties are within the tolerance window(s) (i.e., "no" at step S6-2), the flow can proceed to step S6-4 where component evaluation system 220 evaluates component(s) 102, 104, 110, 126, 128 as not posing a risk (e.g., not including a possible defect, not being in need of service or replacement, etc.). The alternative steps S6-3 and S6-4 provide two example evaluations for component(s) 102, 104, 110, 126, 128, hut it is understood that other evaluations are possible (e.g., posing a partial risk, low risk, high risk, etc.) are possible based on the number of acoustic signatures in industrial plant 152 which exceed particular tolerance windows. As discussed elsewhere herein, the flow can end ("Done") after the condition of component(s) 102, 104, 110 in step S6 concludes.

Evaluating the condition of component(s) 102, 104, 110, 126, 128 within industrial plant 152 can include determining, at step S6-5 one or more operating attributes of component(s) 102, 104, 110, 126, 128 which correspond to the detected acoustic signatures 166. An operating attribute of a component is defined elsewhere herein as one or more metrics, other than a waveform representing acoustic signature(s) 166, which quantifying the performance of component(s) 102, 104, 110, 126, 128. The operating attributes of a component can he obtained from other components of computing device 200 independent from system 150 and/or from other currently-known or later-developed devices for measuring, calculating, or otherwise determining the operating attributes of component(s) 102, 104, 110, 126, 128 within industrial plant 152. The determined operating attribute(s) can he recorded as data 300, e.g., within operating attribute field 306. The determining of operating attributes at step S6-5 can occur before, after, or during other process steps described herein. Furthermore, component evaluation system 206 of computing device 200 can be configured to continuously or periodically index the determined operating attributes with acoustic signatures 166 detected in step S2 (FIG. 4). For example, step S6-5 can include determining a percentage difference between an expected power output from turbine component 104 and an actual power output, which may yield, e.g., a reduction in power output of approximately fifty percent. Where operating attribute field 304 defines, e.g., a thirty percent reduction in power output as indicative of a defect in turbine 304, acoustic analysis program 220 can flag turbine 104 and/or other component(s) 102, 110 for an evaluation based on acoustic properties. Where acoustic properties of the flagged component(s) 102, 104, 110, 126, 128 are anomalous, e.g., having a frequency, amplitude, etc., different from a baseline acoustic signature and/or outside one or more thresholds as discussed elsewhere herein, acoustic analysis program can flag one or more component(s) 102, 104, 110, 126, 128 as being defective.

Although the various sub-processes of step S6 may be implemented in parallel, e.g., simultaneously as shown in FIG. 5 and described herein, it is understood that other process flows are contemplated in embodiments of the present disclosure. For instance, determining operating attributes of one or more components 102, 104, 110, 126, 128 in step S6-5 can occur before or after locating the position of component(s) 102, 104, 110, 126, 128 in step S6-1, and/or comparing acoustic signature(s) 166 with tolerance window(s) in steps S6-2, S6-3, S6-4, etc. In addition, it is understood that the various sub-processes of step S6 depicted in FIG. 5 may be performed partially or entirely sequentially, e.g., by implementing steps S6-1, S6-2, S6-3, S6-4, and S6-5 in their numerical order, reverse numerical order, a partially shuffled order, etc. One or more of the various sub-processes of step S6 described herein may also be omitted where desirable and/or applicable.

Technical effects of the systems and methods disclosed herein can include an infrastructure with hardware and/or software for providing acoustic analysis of components 102, 104, 110, 126, 128 (e.g., of a turbomachine 100 FIG. 1) within an industrial plant 152 which can be embedded at least partially within lighting devices 164. In addition, embodiments of system 150 and/or alternative infrastructures can interface with other systems for measuring and/or evaluating attributes of components 102, 104, 110, 126, 128 to provide a robust solution for identifying and/or treating possible risks within industrial plant 152.

The system with its data storage system (4D point cloud) can be queried following any undetected event to allow the additional algorithms to be created or settings tuned and implemented within the system for future improvements and added detection robustness.

The various embodiments discussed herein can offer several technical and commercial advantages, some of which are discussed herein by way of example. Embodiments of the present disclosure can generally provide a low-cost solution for equipping industrial plants with a system, infrastructure, and/or other product for analyzing acoustic data. In particular, providing a network of acoustic sensors embedded within lighting devices can provide greater coverage of an industrial plant (e.g., a power plant) than may be achievable with conventional acoustic single sensors or multiple point sensor devices. Such coverage can also increase the accuracy and scope of an acoustic analysis. In addition, embodiments of the present disclosure may allow a user (e.g., a plant manager) to access and apply the results of an acoustic analysis using a portal included within a mobile computing device and/or pre-existing system for managing an industrial plant.

The terminology used herein is for the purpose of describing particular embodiments only and is not intended to be limiting of the disclosure, As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system that detects an acoustic signature of a component in an industrial plant and evaluates a condition of the component, wherein the component has an operational performance and a status, the system comprising:
   a first lighting device configured to illuminate an area of the industrial plant;
   a first acoustic sensor embedded within the first lighting device and configured to detect the acoustic signature of the component in the industrial plant; and
   a computing device communicatively connected to the first acoustic sensor and configured to evaluate the condition of the component in the industrial plant based on the acoustic signature, wherein the condition of the component includes the operational performance and the status of the component.

2. The system of claim 1, wherein the computing device is further configured to compare the acoustic signature detected by the first acoustic sensor with a baseline acoustic signature to evaluate the condition of the component.

3. The system of claim 2, wherein the computing device is further configured to determine whether one of an amplitude and a frequency of the acoustic signature is outside a tolerance window of the baseline acoustic signature to evaluate the condition of the component.

4. The system of claim 1, wherein the computing device is further configured to identify the component from a plurality of components based on a directional analysis of the acoustic signature detected by the first acoustic sensor.

5. The system of claim 1, wherein the computing device is further configured to locate a position of the component based on the acoustic signature, a position of the first lighting device, and a position of a second acoustic sensor for detecting the acoustic signature.

6. The system of claim 1, wherein an electric current transmitted to the first lighting device powers the first acoustic sensor.

7. The system of claim 1, wherein the computing device is at least partially included within the first lighting device.

8. The system of claim 1, wherein the computing device evaluates the condition of the component based on an operating attribute of an assembly including the component therein, in addition to the acoustic signature detected by the first acoustic sensor.

9. The system of claim 1, wherein the first lighting device comprises one of a plurality of lighting devices configured to illuminate respective areas of the industrial plant, at least one of the plurality of lighting devices including a respective acoustic sensor therein, and wherein the computing device is communicatively connected to the acoustic sensors in each of the plurality of lighting devices.

10. The system of claim 1, wherein the component is included within a power generation system, and wherein the component includes one of a compressor, a combustor, a generator, and a turbine component of the power generation system.

11. A method for evaluating a condition of a component in an industrial plant, where the component has an operational performance and a status, the method comprising:
    detecting an acoustic signature of the component in the industrial plant with a first acoustic sensor included within a first lighting device of the industrial plant;
    determining a difference between a baseline acoustic signature and the acoustic signature of the component in the industrial plant;
    identifying the component from a plurality of components based on at least the acoustic signature and a position of the first lighting device; and
    evaluating the condition of the component based on a position of the component and the difference between the acoustic signature and the baseline acoustic signature, wherein the condition of the component includes the operational performance and the status of the component.

12. The method of claim 11, wherein the evaluating the condition of the component further includes determining whether one of an amplitude and a frequency of the acoustic signature is outside a tolerance window of the baseline acoustic signature.

13. The method of claim 11, wherein the identifying the component includes locating a position of the component based on the acoustic signature, the position of the first lighting device, and a position of a second acoustic sensor for detecting the acoustic signature.

14. The method of claim 11, wherein the component is included within a power generation system, and wherein the component includes one of a compressor, a combustor, a generator, and a turbine component of the power generation system.

15. The method of claim 11, wherein the evaluating of the condition of the component is further based on an operating attribute of an assembly including the component.

16. The method of claim 15, wherein the evaluating of the condition of the component is further based on a video feed of the component recorded substantially contemporaneously with the acoustic signature of the component.

17. The method of claim 13, wherein the determining, the locating, and the evaluating are performed with a computing device communicatively connected to the first acoustic sensor, and wherein the computing device is at least partially included within the first lighting device.

18. A program product stored on a computer readable storage medium for evaluating a condition of a component in an industrial plant, wherein the component has an operational performance and a status, the computer readable storage medium comprising program code for causing a computer system to:

determine a difference between a baseline acoustic signature and an acoustic signature of the component in the industrial plant, the acoustic signature of the component being detected by a first acoustic sensor included within a first lighting device of the industrial plant;

identify the component from a plurality of components based on at least the acoustic signature and a position of the first lighting device; and evaluate the condition of the component based on a position of the component and the difference between the acoustic signature and the baseline acoustic signature, wherein the condition of the component includes the operational performance and the status of the component.

19. The program product of claim 18, wherein the computer system and the first acoustic sensor is included within the first lighting device, and wherein the computer system is communicatively connected to a second acoustic sensor included in a second lighting device of the industrial plant.

20. The program product of claim 18, further comprising program code for causing the computer system to evaluate the condition of the component further based on historical data generated from a previous operation of the industrial plant.

* * * * *